United States Patent

Oba et al.

[11] 4,383,996
[45] May 17, 1983

[54] DERIVATIVE OF THIAZOLO[3,2-a]PYRIMIDINE AND A PROCESS FOR THE PREPARATION THEREOF AND A DRUG CONTAINING IT

[75] Inventors: Takeo Oba; Kiyoshi Bannai; Toshio Tanaka; Kenzo Watanabe; Tatsuyuki Naruchi; Keiji Komoriya; Seizi Kurozumi; Kenji Hoshina, all of Hino, Japan

[73] Assignee: Teijin Limited, Osaka, Japan

[21] Appl. No.: 339,460

[22] PCT Filed: Apr. 28, 1980

[86] PCT No.: PCT/JP80/00090
§ 371 Date: Dec. 28, 1981
§ 102(e) Date: Dec. 28, 1981

[87] PCT Pub. No.: WO81/03174
PCT Pub. Date: Nov. 12, 1981

[51] Int. Cl.³ .................. C07D 513/04; A61K 31/505
[52] U.S. Cl. ..................................... 424/251; 544/278
[58] Field of Search ....................... 544/278; 424/251

[56] References Cited

FOREIGN PATENT DOCUMENTS

| 55-64591 | 5/1980 | Japan | 544/278 |
| 55-64592 | 5/1980 | Japan | 544/278 |
| 55-66592 | 5/1980 | Japan | 544/278 |
| 55-133754 | 5/1980 | Japan | 544/278 |
| 55-136293 | 10/1980 | Japan | 544/278 |
| 638504 | 6/1950 | United Kingdom | 544/278 |

OTHER PUBLICATIONS

Masters, E. J., et al., JACS, 64, 2709–2711 (1942).

*Primary Examiner*—Donald G. Daus
*Assistant Examiner*—Sharon A. Gibson
*Attorney, Agent, or Firm*—Sughrue, Mion, Zinn, Macpeak & Seas

[57] ABSTRACT

A derivative of thiazolo [3,2-a] pyrimidine expressed by formula (I)

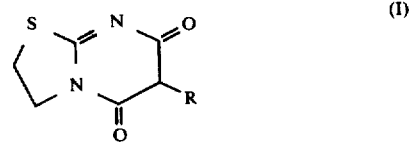

(where R indicates a phenyl group or a benzyl group which has a halogen atom, a lower alkyl or lower alkyloxy group as a substituent group, an alicyclic group or an arylethyl group), and a process for the preparation of a compound of formula (I) comprising cyclizing a compound expressed by formula (II) by application of heat

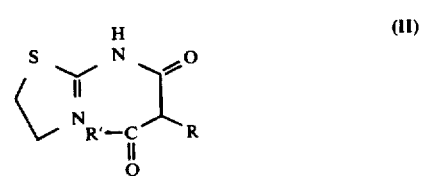

(where a definition of R is as same as that given in case of formula (I) and R' indicates a halogen atom or lower alkyloxy group). A drug which contains this compound as active ingredient is useful for curing autoimmune diseases such as rheumatoid arthritis, nephritis, etc.

6 Claims, No Drawings

DERIVATIVE OF THIAZOLO[3,2-a]PYRIMIDINE AND A PROCESS FOR THE PREPARATION THEREOF AND A DRUG CONTAINING IT

TECHNICAL FIELD

The present invention relates to a novel derivative of thiazolo[3,2-a]pyrimidine, a drug which contains it, and a process for the preparation of said derivative of thiazolo[3,2-a]pyrimidine. More particularly, the present invention relates to a novel derivative of thiazolo[3,2-a]pyrimidine having excellent immunoregulating activities which is especially effective in curing such autoimmune diseases as nephritis, rheumatoid arthritis, etc. and a process for the preparation thereof and an immunoregulating drug which contains said derivative as an active ingredient.

BACKGROUND ART

In recent years, immunoregulating therapy has come to be practiced to cure such autoimmune diseases as rheumatoid arthritis, generalized lupus erythematodes, etc. or malignant tumor and a variety of drugs have been developed. As an example of such drugs, the application of levamisole, which is a levorotatory isomer of tetramisole, to the drugs for immunotherapy of cancer and such autoimmune diseases as rheumatoid arthritis has due attention.

Though it has been reported that levamisole has efficacy in said diseases to a certain degree, it has no singularity in its efficacy and does not always display its efficacy satisfactorily either. Many immunoregulating drugs have been developed but most of them not only lack singularity in their remedial activities but also raise a problem of side effects, and no satisfactory drugs of this kind are available as yet.

Meanwhile, it is mentioned in the "Journal of American Chemical Society" vol. 64, pp. 2709–2712, 1942, that a derivative of barbituric acid is obtained from 2-aminothiazoline and diethyl malonate, and that this compound has a hypnotic action and an anesthetic action as well; however, nothing is mentioned in the journal as to other efficacy besides its hypnotic and anesthetic actions.

The inventors of the present invention have prepared a novel thiazolo[3,2-a]pyrimidine derivative which is a novel barbituric acid derivative different from the derivative of barbituric acid mentioned in the above journal and made a focused study of the efficacy of this newly prepared compound. The result is a remarkable finding that it is a compound which has a specific immunoregulating action different from an action owned by levamisole, or the immunoregulating action based on a pharmacological action apart from hypnotic and anesthetic actions, and that, because of its low toxicity, the abovementioned thiazolo[3,2-a]pyrimidine derivative is very useful for curing such autoimmune diseases as rheumatoid arthritis, nephritis, etc., thus producing the present invention.

DISCLOSURE OF INVENTION

The present invention is directed to a derivative of thiazolo[3,2-a]pyrimidine expressed by the following formula (I)

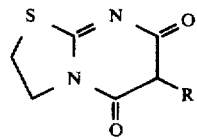

(where R indicates a phenyl group or a benzyl group which has a halogen atom, a lower alkyl or lower alkyloxy group as a substituent group, an alicyclic group or an arylethyl group), and a process for the preparation of the derivative of thiazolo[3,2-a]pyrimidine expressed by the following formula (I)

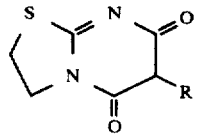

(where a definition of R is as same as that given in case of the abovementioned formula (I), comprising cyclizing a compound expressed by the following formula (II) by application of heat

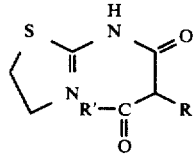

(where R indicates a phenyl group or a benzyl group which has a halogen atom, a lower alkyl or lower alkyloxy group as a substituent group, an alicyclic group or an arylethyl group, and R' indicates a halogen atom or lower alkyloxy group), and an immunoregulating drug which contains the derivative of thiazolo[3,2-a]pyrimidine expressed by the abovementioned formula (I) as an active ingredient.

BEST MODE OF CARRYING OUT THE INVENTION

R of the derivative of thiazolo[3,2-a]pyrimidine expressed by the aforementioned formula (I) of the present invention is a phenyl group or a benzyl group which has a halogen atom, a lower alkyl or lower alkyloxy group as a substituent group, an alicyclic group or an arylethyl group.

As a phenyl group or a benzyl group which has a halogen atom, lower alkyl or lower alkyloxy group as a substituent group, there are such phenyl groups as p-chlorophenyl, o-chlorophenyl, m-chlorophenyl, p-fluorophenyl, m-fluorophenyl, o-fluorophenyl, p-bromophenyl, m-bromophenyl, o-bromophenyl, etc. which have a halogen atom as a substituent group; such phenyl groups as p-tolyl, o-tolyl, o-ethylphenyl, m-isopropylphenyl, p-butylphenyl, etc. which have a lower alkyl group as a substituent group; such phenyl groups as o-methoxyphenyl, p-ethoxyphenyl, m-propoxyphenyl, etc. which have a lower alkyloxy group as a substituent group; such benzyl groups as p-chlorobenzyl, o-chlorobenzyl, m-chlorobenzyl, p-fluorobenzyl, o-fluorobenzyl, m-fluorobenzyl, p-bromobenzyl, m-bromobenzyl, o-bromobenzyl, etc. which have a halogen atom as a substituent group; such benzyl groups as p-methylbenzyl, o-ethylbenzyl, m-isopropylbenzyl, etc. which have a lower alkyl group as a substituent group; and such benzyl groups as o-methoxybenzyl, p-ethoxybenzyl, m-propoxybenzyl, etc. which have a lower alkyloxy group as a substituent group.

As an alicyclic group, there are cyclopropyl, cyclobutyl, cyclopentyl, cycloheptyl, cyclohexyl, and 2-methylcyclopropyl.

As an arylethyl group, there are phenethyl group and pyridylethyl group.

Of these groups mentioned above, it is preferable to select R from such phenyl groups or benzyl groups as p-chlorophenyl, o-chlorophenyl, m-chlorophenyl, p-chlorobenzyl, o-chlorobenzyl, m-chlorobenzyl, p-fluorophenyl, m-fluorophenyl, o-fluorophenyl, p-fluorobenzyl, o-fluorobenzyl, m-fluorobenzyl, p-bromophenyl, m-bromophenyl, o-bromophenyl, p-bromobenzyl, m-bromobenzyl, and o-bromobenzyl which have a chlorine atom, fluorine atom, or bromine atom as a substituent group respectively, a cyclohexyl group or a phenethyl group.

It is especially preferable to select R from such chlorobenzyl groups and chlorophenyl groups as p-chlorobenzyl, o-chlorobenzyl, p-chlorophenyl and o-chlorophenyl.

A derivative of thiazolo[3,2-a]pyrimidine of the present invention may be of enol form and a derivative of enol form has the same pharmacological activity.

Also said derivative may take the form of acid addition salt of an inorganic acid or an organic acid. As an inorganic acid, there are hydrochloric acid, hydrobromic acid, and hydroiodic acid, and as an organic acid, there are acetic acid, propionic acid, lactic acid, and maleic acid, for instance.

A derivative of thiazolo[3,2-a]pyrimidine expressed by said formula (I) can be prepared by cyclizing a compound expressed by the following formula (II) by application of heat

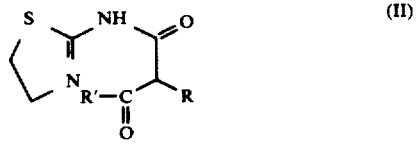

(where R indicates a phenyl group or benzyl group which has a halogen atom, a lower alkyl or lower alkyloxy group as a substituent group, an alicyclic group or an arylethyl group, and R' indicates a halogen atom or lower alkyloxy group).

R of the above formula (II) is the same R as in the aforementioned formula (I).

R' is a halogen atom such as bromine, iodine, chlorine etc. or a lower alkyloxy group such as methoxy, ethoxy, etc.

The cyclization of a compound expressed by the abovementioned formula (II) by application of heat may be conducted either with the use of a solvent or in the absence of a solvent. In the cyclization in which a solvent is used, toluene, xylene, cumene, cymene, tetralin, decalin, diethylene glycol dimethyl ether, diethylene glycol diethyl ether, diethylene glycol dibutyl ether, diphenyl ether, dimethyl sulfoxide, dimethylformamide, nitrobenzene, etc. may be mentioned as recommendable solvents. The amount of such solvents to be used is usually in the range of 1 to 1,000 times the molar quantity of the material compound.

Though the reaction temperature and time vary depending upon the starting material, presence or absence of a solvent, kind of the solvent, the desired derivative of thiazolo[3,2-a]pyrimidine is usually obtained by conducting the reaction at 80° to 320° C. for 1 minute to 48 hours.

A compound expressed by the aforementioned formula (II) can be obtained, for instance, by making 2-aminothiazoline expressed by the following formula (III)

react with a compound expressed by the following formula (IV) while heating

(where R indicates a phenyl group or a benzyl group which has a halogen atom, a lower alkyl or lower alkyloxy group as a substituent group, an alicyclic group or an arylethyl group, and R' indicates a halogen atom or lower alkyloxy group).

In the abovementioned formula (IV), R is the same R as defined in the aforementioned formula (I) and R' is the same R' as defined in the aforementioned formula (II).

The abovementioned reaction may be carried out with the use of a solvent or no solvent. In case where a solvent is used, the kinds of solvents and their amounts to be used can be the same solvents and amounts as mentioned for cyclizing a compound expressed by the aforementioned formula (II) by heating.

As for the method for the preparation of a derivative of thiazolo[3,2-a]pyrimidine of the present invention, it is preferable first to make a compound expressed by the aforementioned formula (III) react with a compound expressed by the aforementioned formula (IV) while heating to obtain a compound expressed by the aforementioned formula (II), and, without isolating this compound expressed by formula (II), further let the reaction continue with heating to obtain a derivative of thiazolo[3,2-a]pyrimidine of the present invention.

A derivative of thiazolo[3,2-a]pyrimidine expressed by said formula (I) is especially used for curing such autoimmune diseases as rheumatoid arthritis, nephritis, etc. and is administered orally, or nonorally by way of the rectum, subcutaneous, muscle, etc.

For oral administration, the drug is prepared in the form of a solid preparation or a liquid preparation. As a solid preparation, there are a tablet, pill, powder, and granule. In preparing these solid preparations, one or more derivatives of thiazolo[3,2-a]pyrimidine are used as active ingredients and they are mixed with at least one inactive diluent such as commonly used calcium carbonate, potato starch, alginic acid and lactose. The preparation is carried out according to the ordinary method and addition agents other than a diluent, for instance, such a lubricant as magnesium stearate may be contained in them.

Liquid preparations for oral administration use contain pharmaceutically permissible emulsifier, solvent, suspension, syrup, etc. and commonly used inactive diluents such as water and liquid paraffin.

These preparations contain other auxiliary agents such as a wetting agent, auxiliary suspending agent, sweetening agent, flavoring agent, aromatic, and preservative in addition to said inactive diluents.

Also these liquid preparations may be enclosed in capsules made from such an assimilable substance as gelatin.

As a solid preparation for rectum administration use, a suppository, which contains one or more active principles and is prepared according to a publicly known method, may be mentioned.

Preparations to be administered nonorally include aseptically prepared aqueous and nonaqueous solution, suspension, and emulsion. As solvent or suspending agent for nonaqueous preparation use, there are propylene glycol, polyethylene glycol, vegetable oil such as olive oil, and injectable organic ester such as ethyl oleate. These preparations may also contain such auxiliary agents as a preservative, wetting agent, emulsifying agent, and dispersing agent. These preparations can be made aseptic by filtration through a bacterial filter, or by addition of a bactericide, or by irradiation. An aseptic solid preparation prepared beforehand may be used by dissolving it in aseptic water or aseptic injectionable solvent immediately before its administration.

The dosage of a derivative of thiazolo[3,2-a]pyrimidine is 0.1 to 50 mg/Kg, especially preferable in the range of 0.5 to 20 mg/Kg; however, the dosage varies depending upon the condition of the disease and age of a patient and the method of administration.

The present invention is illustrated for further details but not limited by the following examples.

EXAMPLE 1

A mixture consisting of 1.0 g of 2-aminothiazoline and 2.4 g of cyclohexyl diethyl malonate was made to react in a stream of nitrogen for 30 minutes while heating at 180° C. After the reaction product was allowed to cool down to room temperature, it was chromatographed on a column of silica gel and was developed with ethyl acetate-benzene (1:4) to obtain 2.01 g of desired 6-cyclohexyl-5H-2,3,6,7-tetrahydro-5,7-dioxothiazolo[3,2-a]pyrimidine (yield: 80%). The properties of this matter were as follows:

Melting point: 250° to 251° C.

IR $(\nu_{max}^{KBr})$ cm$^{-1}$: 3200–2500 (enol form), 1655, 1525, 1426, 1321, 705.

NMR $(\delta_{TMS}^{DMSO-d6})$: 1.0–2.0 (11H, m), 3.50 (2H, t, J=8 Hz), 4.33 (2H, t, J=8 Hz), 11.0 (1H, br, D$_2$O, disappeared).

EXAMPLE 2

A mixture consisting of 1.02 g of 2-aminothiazoline and 3.0 g of p-chlorophenyl diethyl malonate was heated at 180° C. for 30 minutes to carry out the reaction. After the reaction product was allowed to cool down to room temperature, 30 ml of ether was added thereto, and the precipitated crystals were filtered off to obtain 1.7 g of desired 6-p-chlorophenyl-5H-2,3,6,7-tetrahydro-5,7-dioxothiazolo[3,2-a]pyrimidine (yield: 63%). The properties of this matter were as follows:

Melting point: 275° C.

IR $(\nu_{max}^{KBr})$ cm$^{-1}$: 3100–2600 (enol form), 1645, 1590, 1528, 1437, 1390.

NMR $(\delta_{TMS}^{DMSO-d6})$: 3.75 (2H, t, J=8 Hz), 4,43 (2H, t, J=8 Hz), 7.4 (4H, m), 11.5 (1H, br).

EXAMPLE 3

A mixture consisting of 1.5 g of 2-aminothiazoline and 4.5 g of p-chlorobenzyl diethyl malonate was made to react in a stream of nitrogen for 2 hours while heating at 180° C. 8 ml of diphenyl ether was added to the obtained solid reaction product and the mixture was further made to react in a stream of nitrogen while heating at 220° C. for 2 hours. The product resulting from the reaction was allowed to cool down to room temperature, chromatographed on a column of silica gel and eluted with chloroform-methanol (96:4) to obtain 1.8 g of desired 6-p-chlorobenzyl-5H-2,3,6,7-tetrahydro-5,7-dioxothiazolo[3,2-a]pyrimidine (yield: 38%). The properties of this matter were as follows:

Melting point: 273.5°–275.5° C.

IR $(\nu_{KBr}^{max})$ cm$^{-1}$: 3100–2300 (enol form), 1655, 1640, 1625, 1545, 1445, 1403, 1289, 1110, 1098, 800.

NMR $(\delta_{TMS}^{DMSO-d6})$: 3.48 (br, t, J=8 Hz), 3.52 (s), 4.28 (2H, br, t, J=8 Hz), 7.26 (4H, s), 9.30 (1H, br).

EXAMPLE 4

A mixture consisting of 0.5 g of 2-amino-thiazoline and 1.5 g of o-chlorobenzyl diethyl malonate was made to react in a stream of nitrogen for 1.5 hours while heating at 170° C. The reaction product thus obtained was chromatographed on a column of silica gel and eluted with chloroform-methanol (97–90:3–10) to give 0.86 g of desired 6-(o-chlorobenzyl)-5H-2,3,6,7-tetrahydro-5,7-dioxothiazolo[3,2-a]pyrimidine (yield: 45%). The properties of this matter were as follows:

Melting point: 265°–274° C.

IR $(\nu_{KBr}^{max})$ cm$^{-1}$: 3100–2300 (enol form), 1650, 1620, 1528, 1440, 1400, 1100, 1038, 748.

NMR $(\delta_{TMS}^{DMSO-d6})$: 3.52 (t, J=8 Hz), 3.62 (2H, s), 4.33 (2H, t), 7.2 (4H, m), 11.63 (1H, br).

EXAMPLE 5

A mixture consisting of 2.0 g of 2-aminothazoline and 5.8 g of phenthyl diethyl malonate was made to react in a stream of nitrogen for 1.5 hours while heating at 180° C. 8 ml of diphenyl ether was added to thus obtained oily product and the mixture was again made to react in a stream of nitrogen for 1.5 hours while heating at 220° C. The obtained reaction product was put to column chromatography on silica gel and eluted with chloroform-methanol (90–95:10–5) to give 2.74 g of desired 5H-2,3,6,7-tetrahydro-5,7-dioxo-6-phenethyl-thiazolo[3,2-a]pyrimidine (yield: 51%). The properties of this matter were as follows:

Melting point: 253°–263° C.

IR $(\nu_{KBr}^{max})$ cm$^{-1}$: 3200–2300 (enol form), 1640, 1605, 1515, 1400, 1150, 1100, 752.

NMR $(\delta_{TMS}^{DMSO-d6})$: 2.56 (4H, s), 3.47 (2H, t, J=8 Hz), 4.27 (2H, t, J=8 Hz), 7.20 (5H, s).

EXAMPLE 6

A mixture consisting of 0.5 g of 2-aminothiazoline and 1.3 g of p-methylbenzyl diethyl malonate was made to react in a stream of nitrogen for 2 hours while heating at 180° C. The reaction product was then put to column chromatography on silica gel and eluted with chloroform-methanol (99:1) to obtain 0.6 g of desired 5H-2,3,6,7-tetrahydro-6-p-methylbenzyl-5,7-dioxothiazolo[3,2-a]pyrimidine (yield: 44%). The properties of this matter were as follows:

Melting point: 267°–268.5° C.

IR $(\nu_{max}^{KBr})$ cm$^{-1}$: 3200–2610 (enol form), 1640, 1615, 1530, 1440, 1400, 1287, 1096, 802, 786.

NMR $(\delta_{TMS}^{DMSO-d6})$: 2.28 (3H, s), 3.53 (2H, s), 3.53 (2H, t, J=8 Hz), 4.38 (2H, t, J=8 Hz), 7.28 (4H, s), 10.7 (1H, br).

EXAMPLE 7

5H-2,3,6,7-tetrahydro-6-p-methoxybenzyl-5,7-dioxothiazolo[3,2-a]pyrimidine was obtained according to the same method as Example 6. The properties of this matter were as follows:

Yield: 39%.

Melting point: 228°–230° C.

IR $(\nu_{max}^{KBr})$ cm$^{-1}$: 3400–2650 (enol form), 1640, 1610, 1530, 1505, 1435, 1280, 1240, 1100, 1022, 800.

NMR $(\delta_{TMS}^{DMSO-d6})$: 3.57 (2H, s), 3.59 (2H, t, J=8 Hz), 3.76 (3H, s), 4.38 (2H, t, J=8 Hz), 6.87 (2H, d, J=9 Hz), 7.27 (2H, d, J=9 Hz), 11.3–11.7 (1H, br, D$_2$O, disappeared).

EXAMPLE 8

5H-2,3,6,7-tetrahydro-6-o-methoxybenzyl-5,7-dioxothiazolo[3,2-a]pyrimidine was obtained according to the same method as Example 6. The properties of this matter were as follows:

Yield: 55%.

Melting point: 259°–260.5° C.

IR $(\nu_{max}^{KBr})$ cm$^{-1}$: 3400–2570 (enol form), 1653, 1595, 1515, 1446, 1345, 1293, 1208, 1090, 777, 758, 742, 722.

NMR $(\delta_{TMS}^{DMSO-d6})$: 3.56 (2H, t, J=8 Hz), 3.61 (2H, s), 3.88 (3H, s), 4.40 (2H, t, J=8 Hz), 6.7–7.5 (4H, m), 11.0 (1H, br).

EXAMPLE 9

6-p-fluorobenzyl-5H-2,3,6,7-tetrahydro-5,7-dioxothiazolo[3,2-a]pyrimidine was obtained according to the same method as Example 6. The properties of this matter were as follows:

Yield: 58%

Melting point: 267°–268° C.

IR $(\nu_{max}^{KBr})$ cm$^{-1}$: 3500–2630 (enol form), 1625, 1540, 1500, 1442, 1405, 1287, 1212, 1105, 820, 790, 737.

NMR $(\delta_{TMS}^{DMSO-d6})$: 3.54 (2H, t, J=8 Hz), 3.59 (2H, s), 4.37 (2H, t, J=8 Hz), 6.9–7.6 (4H, m), 11.5–11.9 (1H, br, D$_2$O, disappeared).

EXAMPLE 10

5H-2,3,6,7-tetrahydro-6-p-methoxyphenyl-5,7-dioxothiazolo[3,2-a]pyrimidine was obtained according to the same method as Example 6. The properties of this matter were as follows:

Yield: 18%.

Melting point: 266°–268° C.

IR $(\nu_{max}^{KBr})$ cm$^{-1}$: 3400–2650 (enol form), 1642, 1600, 1570, 1555, 1425, 1395, 1290, 1245, 1180, 1138, 1062, 1028, 952, 860, 835, 821, 776, 742.

NMR $(\delta_{TMS}^{DMSO-d6})$: 3.55 (2H, t, J=7 Hz), 3.75 (3H, s), 4.35 (2H, t, J=7 Hz), 6.7–7.6 (4H, m), 11.3–11.7 (1H, br, D$_2$O, disappeared).

EXAMPLE 11

5H-2,3,6,7-tetrahydro-6-O-methoxyphenyl-5,7-dioxothiazolo[3,2-a]pyrimidine was obtained according to the same method as Example 6. The properties of this matter were as follows:

Yield: 27%.

Melting point: 256°–258° C.

IR $(\nu_{max}^{KBr})$ cm$^{-1}$: 3400–3100 (enol form), 1620, 1592, 1510, 1400, 1275, 1140, 1110, 1060, 1045, 1023, 790, 747.

NMR $(\delta_{TMS}^{DMSO-d6})$: 3.54 (2H, t, J=7 Hz), 3.68 (3H, s), 4.35 (2H, t, J=7 Hz), 6.9–7.5 (4H, m), 10.6 (1H, br).

EXAMPLE 12

5-H-2,3,6,7-tetrahydro-5,7-dioxo 6-p-bromophenylthiazolo[3,2-a]pyrimidine was obtained according to the same method as Example 6, having the following properties:

Yield: 48%.

Melting point: 284°–287° C.

IR $(\nu_{max}^{KBr})$ cm$^{-1}$: 3200–2200 (enol form), 1640, 1540, 1430, 1380, 1300, 1225, 1138, 1058, 1008, 950, 825.

NMR $(\delta_{TMS}^{DMSO-d6})$: 3.55 (2H, t, J=8 Hz), 4.35 (2H, t, J=8 Hz), 7.50 (4H, s), 10.5 (1H, br).

EXAMPLE 13

In this example the immunoregulating actions of the undermentioned compounds obtained in Examples 1 to 5 and Example 9 were examined with the results shown herein:

6-cyclohexyl-5H-2,3,6,7-tetrahydro-5,7-dioxothiazolo[3,2-a]pyrimidine (hereinafter referred to as medicine A), 6-p-chlorophenyl-5H-2,3,6,7-tetrahydro-5,7-dioxothiazolo[3,2-a]pyrimidine (hereinafter referred to as medicine B), 6-p-chlorobenzyl-5H-2,3,6,7-tetrahydro-5,7-dioxothiazolo[3,2-a]pyrimidine (hereinafter referred to as medicine C), 6-(o-chlorobenzyl)-5H-2,3,6,7-tetrahydro-5,7-dioxothiazolo[3,2-a]pyrimidine (hereinafter referred to as medicine D), 5H-2,3,6,7-tetrahydro-5,7-dioxo-6-phenethylthiazolo[3,2-a]pyrimidine (hereinafter referred to as medicine E), and 6-p-fluorobenzyl-5H-2,3,6,7-tetrahydro-5,7-dioxothiazolo[3,2-a]pyrimidine (hereinafter referred to as medicine F).

(i) Effect on delayed-type hypersensitivity:

The effect of the medicines was estimated with an index of delayed-type hypersensitivity which is caused by injecting red sheep blood cells as antigen into the pads of mice (see the method described by P. H. Lagrange, G. B. Mackaness, and T. E. Mille, Journal of Experimental Medicine, Vol.139, pp.1529–1539, 1974; Immunology, Vol.34, p.363,1978).

Groups consisting of 4 or 5 C3H/He male mice (7 weeks old) were used in the experiments. The mice were sensitized by injecting 10$^6$ red sheep blood cells suspended in 0.2 ml of physiological saline intravenously into the tail vein. Then the mice were administered orally with the abovementioned medicines in doses mentioned in Table 1 immediately after the sensitization, 1 day after the sensitization, 2 days after the sensitization, and 3 days after the sensitization respectively. 24 hours after the oral administration of the medicines made 3 days after the sensitization, 10$^8$ sheep red blood cells suspended in 25 μl of physiological saline were injected subcutaneously dermically into the right hind foot pad of the mice to induce a hypersensitivity. 24 hours after the induction of the allergic reaction, the thickness of the pad was measured with a micrometer to determine the increase in thickness (foot pad reaction 0.1 mm) as compared with the thickness of the pad before the subcutaneous injection of 10$^8$ sheep red blood cells thus to know the effect of the medicines on the delayed-type hypersensitivity.

For the purpose of comparison, experiments were conducted with the mice which were not given the medicines and with those which were administered with levamisole and D-penicillamine respectively in the place of the medicines of the present invention. The results of these experiments are shown in Table 1.

TABLE 1

| | Medicine | Dose (mg/Kg) | Number of cases | Foot pad reaction (0.1 mm) |
|---|---|---|---|---|
| Experiment 1 | Control | — | 8 | 3.1 ± 0.5 |
| | Medicine C | 0.3 | 4 | 4.1 ± 0.2 |
| | " | 1 | " | 4.9 ± 0.5* |
| | " | 3 | 5 | 4.3 ± 0.4 |
| | " | 10 | " | 4.1 ± 0.7 |
| | Levamisole | 1 | " | 4.3 ± 0.4 |
| | " | 3 | " | 4.6 ± 0.3 |
| | " | 10 | 4 | 5.1 ± 0.3* |
| | D-penicillamine | 1 | 5 | 5.0 ± 0.6 |
| | " | 3 | " | 5.3 ± 0.4** |
| | " | 10 | " | 3.7 ± 0.3 |
| Experiment 2 | Control | | 8 | 4.7 ± 0.7 |
| | Medicine C | 1 | 5 | 7.2 ± 0.5* |
| | " | 5 | " | 6.7 ± 0.7 |
| | " | 25 | " | 6.5 ± 0.4 |
| | Medicine B | 1 | 4 | 5.3 ± 0.8 |
| | " | 5 | " | 5.7 ± 0.5 |
| | Medicine D | 25 | " | 5.7 ± 1.0 |
| | " | 1 | 5 | 6.9 ± 0.9 |
| | " | 5 | 4 | 6.9 ± 1.0 |
| | " | 25 | 5 | 6.1 ± 1.2 |
| | Levamisole | 1 | 4 | 7.6 ± 0.4* |
| | " | 5 | " | 5.9 ± 0.3 |
| | " | 25 | 5 | 6.8 ± 1.0 |
| Experiment 3 | Control | | 4 | 4.7 ± 1.1 |
| | Medicine A | 1 | " | 6.3 ± 1.0 |
| | " | 10 | " | 6.2 ± 1.3 |
| | Medicine E | 1 | " | 4.0 ± 0.8 |
| | " | 10 | " | 5.8 ± 0.7 |
| Experiment 4 | Control | | 5 | 3.0 ± 0.1 |
| | Meidcine F | 1 | " | 5.7 ± 0.5** |
| | " | 3 | " | 3.9 ± 0.4 |

*P < 0.05,
**P < 0.01

It is evident from Table 1 that the medicines according to the present invention are as effective as levamisole and D-penicillamine in increasing the thickness of the kind foot pad of mice (foot pad reaction), in other words, in accelerating the delayed-type hypersensitivity, which proves that the medicines of the present invention have a function to enhance the immunizing action.

(ii) Effect on lymphocyte blast cell transformation (a) The experiments were made according to the method described in the Journal of Immunology, Vol. 122, pp 1–7, 1979 to study the effect of the medicines on the highly exasperated state of immunizing function created by adding a mitogen, which is a cell proliferating factor, to spleen cells obtained from mice to accelerate the cell division.

In the experiments, spleen cells obtained from normal BAL B/c female mice (7 to 8 weeks old) were suspended in a culture medium (RPMI-1640) containing 5% fetus calf serum (FCS). Then a mitogen (concanavalin A or lipopolysaccharide) and the medicine dissolved in dimethyl sulfoxide were added to the culture medium of spleen cells ($10^5$/100 ($10^5$/100 μl). The cells were incubated in the microculture plate in a 95% air, 5% $CO_2$ atmosphere at 37° C. After the 3-day incubation was over, 3H-thymidine (0.5 μl Ci/20 μl) was added thereto and the incubation was conducted for another 18 hours. 3H-thymidine incorporated into the cells was determined with a liquid scintillation counter.

For the purpose of comparison, experiments were conducted likewise with the cells to which the medicine or mitogen was not added and with those to which levamisole and D-penicillamine were added respectively in the place of the medicines of the present invention. The results of these experiments are shown in Table 2.

TABLE 2

| Medicine | Concentration (μg/ml) | Mitogen (μg/ml) | | | | |
|---|---|---|---|---|---|---|
| | | 0 | Concanavalin A | | Lipopolysaccharide | |
| | | | 0.25 | 5 | 10 | 50 |
| Medicine C | 0 | 193 ± 17 | 4985 ± 802 | 22460 ± 2742 | 1996 ± 432 | 2644 ± 413 |
| | 1.0 | 143 ± 17 | 3653 ± 192 | 17919 ± 657 | 2167 ± 633 | 1654 ± 243 |
| | 2.5 | 164 ± 4 | 4753 ± 1004 | 13686 ± 1260 | 1371 ± 198 | 1052 ± 82 |
| | 5.0 | 218 ± 40 | 4484 ± 876 | 8568 ± 2009 | 1529 ± 400 | 737 ± 312 |
| Levamisole | 0 | 687 ± 59 | 8835 ± 648 | 24733 ± 1043 | 4906 ± 320 | 4132 ± 508 |
| | 10 | 1377 ± 157 | 11780 ± 922 | 93325 ± 12561 | 15359 ± 2944 | 16667 ± 862 |
| | 25 | 3142 ± 388 | 20365 ± 1337 | 139837 ± 26679 | 48044 ± 6048 | 62257 ± 1144 |
| | 50 | 3473 ± 126 | 24163 ± 1332 | 79916 ± 15075 | 63961 ± 7405 | 69523 ± 4231 |
| D-penicillamine | 0 | 687 ± 59 | 8835 ± 648 | 24733 ± 1043 | 4906 ± 320 | 4132 ± 508 |
| | 1 | 490 ± 81 | 5171 ± 768 | 18657 ± 2176 | 1672 ± 261 | 2670 ± 473 |
| | 10 | 399 ± 26 | 4115 ± 559 | 21824 ± 565 | 1342 ± 266 | 1349 ± 176 |
| | 25 | 359 ± 52 | 3932 ± 513 | 31558 ± 3340 | 1446 ± 320 | 1515 ± 390 |

It is apparent from Table 2 that levamisole has a tendency to accelerate the incorporation of 3H-thymidine in both the case where mitogen is not added and the case where mitogen added, while medicine C of the present invention does not exert much influence on the incorporation of 3H-thymidine in the case where mitogen is not added but it has a tendency to strongly suppress the incorporation of 3H-thymidine in the case where mitogen is added. D-penicillamine shows a tendency somewhat similar to that of medicine C but is rather weak.

The above fact concludes that levamisole has the immunostimulative effect on both cells which have a normal immune activity and cells which have an abnormally stimulated immune activity: on the contrary, the medicines of the present invention exercises no influence on the cells which have a normal immune activity but has an immunosuppressive effect only on cells which have an abnormally stimulated immune activity. Therefore, it is confirmed that the medicines of the present invention are drugs that have a very singular immunoregulative activity.

(b) The experiments were carried out according to the same method as the preceding (a) with the use of NZB/WF, female mice which were made to be spontaneously attacked with systemic lupus erythematosus. The results are shown in Table 3.

TABLE 3

| Medicine | Concentration (μg/ml) | Mitogen (μg/ml) 0 | Concanavalin A 0.25 | Concanavalin A 5 | Lipopolysaccharide 10 | Lipopolysaccharide 50 |
|---|---|---|---|---|---|---|
| Medicine C | 0 | 2137 ± 164 | 16327 ± 1282 | 33411 ± 5150 | 20965 ± 1300 | 26212 ± 2662 |
|  | 1.0 | 1721 ± 364 | 12449 ± 1215 | 27807 ± 4082 | 19319 ± 1386 | 22170 ± 1736 |
|  | 2.5 | 1478 ± 240 | 10498 ± 966 | 22191 ± 865 | 14828 ± 1829 | 14197 ± 2169 |
|  | 5.0 | 1433 ± 133 | 9291 ± 1064 | 19532 ± 115 | 15893 ± 2168 | 10867 ± 2430 |
| Levamisole | 0 | 2880 ± 736 | 15925 ± 1788 | 32465 ± 2205 | 25136 ± 321 | 28834 ± 1544 |
|  | 10 | 5411 ± 257 | 42026 ± 4849 | 65800 ± 7832 | 56054 ± 3101 | 61717 ± 3538 |
|  | 25 | 11775 ± 373 | 61492 ± 5661 | 94057 ± 418 | 89072 ± 3024 | 127316 ± 12956 |
|  | 50 | 18498 ± 3276 | 53202 ± 6127 | 119202 ± 15483 | 109322 ± 9136 | 151299 ± 3331 |
| D-penicillamine | 0 | 2880 ± 736 | 15925 ± 1788 | 32465 ± 2205 | 25136 ± 321 | 28834 ± 1544 |
|  | 1 | 2923 ± 105 | 16999 ± 519 | 35597 ± 5483 | 22175 ± 2705 | 27587 ± 3280 |
|  | 10 | 1853 ± 211 | 25081 ± 2500 | 32047 ± 4296 | 16788 ± 1497 | 23217 ± 728 |
|  | 25 | 1880 ± 648 | 29798 ± 178 | 37527 ± 4740 | 15557 ± 293 | 15880 ± 1491 |

As shown in Table 3, levamisole accelerates the incorporation of 3H-thymidine as in the case of the normal mice in the experiments conducted in (a) disregard of whether mitogen is added or not added to the spleen cells obtained from the mice made diseased, while medicine C of the present invention vigorously suppress the 3H-thymidine incorporation when mitogen is added to the spleen cells obtained from the mice made diseased and also suppress the 3H-thymidine incorporation when mitogen is not added. D-penicillamine also shows a tendency somewhat similar to that of medicine C but is rather weak.

It is also concluded from the above fact that, different from levamisole, medicine C of the present invention has a specific effect to suppress the abnormally accelerated immunogenic action of the cells. Thus it is confirmed that the medicines of the present invention has a very singular immunoregulative activity.

From the preceding (i) and (ii), it is evident that the medicines of the present invention have such singular immunoregulative activities as to accelerate the immunity, to exercise no influence to the cells which have a normal immunizing function, and to suppress the abnormally accelerated immunity.

EXAMPLE 14

This example shows that the medicines of the present invention have the low toxicity.

The acute toxicity of the medicine was determined by use of groups of 6 male ICR mice, 6 weeks old, according to an ordinary method.

The results are shown in Table 4.

TABLE 4

| Medicine | Administration | L D50 (g/Kg) |
|---|---|---|
| 6-p-chlorobenzyl-5H—2,3,6,7-tetrahydro-5,7-dioxothiazolo [3,2-a] pyrimidine | Oral administration | 4 or more |

It is apparent from Table 4 that the toxicity of the medicines of the present invention is very low.

EXAMPLE 15

Tablets consisting of the following components per tablet were prepared:

| | |
|---|---|
| Active ingredient (6-p-chlorobenzyl-5H—2,3,6,7-tetrahydro-5,7-dioxothiazolo [3,2-a] pyrimidine) | 200 mg |
| Lactose | 280 mg |
| Potato starch | 80 mg |
| Polyvinyl pyrrolidone | 11 mg |
| Magnesium stearate | 5 mg |

A mixture of the active ingredient, lactose and potato starch was homogeneously moistured with 20% ethanol solution of polyvinyl pyrrolidone, sieved through a 2.0 mm mesh sieve, dried at 45° C., and sieved again through a 1.5 mm mesh sieve. The granules thus obtained were mixed with magnesium stearate and compressed to give tablets.

The compound obtained in Example 3 was used as an active ingredient to represent the medicines of the present invention.

EXAMPLE 16

Hara gelatin capsules consisting of the following components per capsule were prepared:

| | |
|---|---|
| Active ingredient (6-p-chlorobenzyl-5H—2,3,6,7-tetrahydro-5,7-dioxothiazolo [3,2-a] pyrimidine) | 200 mg |
| Micro-crystalline cellulose | 195 mg |
| Amorphous silicic acid | 5 mg |

The finely powdered active ingredient, microcrystalline cellulose and uncompressed amorphous silicic acid were mixed thoroughly and contained in hard gelatin capsules.

EXAMPLE 17

5 ml ampules consisting of the following components per capsule were prepared:

| | |
|---|---|
| Active ingredient (6-p-chlorobenzyl-5H—2,3,6,7-tetrahydro-5,7-dioxothiazolo [3,2-a] pyrimidine) | 200 mg |
| Polyethylene glycol 600 | 200 mg |
| Distilled water  To make a total of | 5.0 ml |

Polyethylene glycol and the active ingredient were dissolved in water in an atmosphere of nitrogen, boiled, cooled in an atmosphere of nitrogen, and distilled. Pretreated water was added to thus obtained solution to make a prescribed volume and filtered under the aseptic conditions. The preparation was conducted in the diffused light.

The filling up was conducted in a stream of nitrogen and the sterilization was carried out at 121° C. for 20 minutes.

INDUSTRIAL APPLICATION

Since the derivatives of thiazolo[3,2-a]pyrimidine of the present invention have singular and excellent immunoregulating activities, they can be used for curing such autoimmune diseases as rheumatoid arthritis, systemic lupus erythematodes, nephritis, nephrosis, Behçet disease, Chrohn disease, idiopathic ulcerative colitis, polyneuritis, fibrosis of the lung, autoimmune hemolytic anemia, uveitis, etc.

We claim:

1. A thiazolo[3,2-a]pyrimidine compound expressed by the following formula (I)

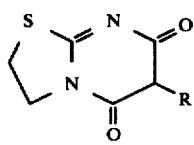

where R represents a phenyl group or a benzyl group which has a halogen atom, a lower alkyl group or a lower alkyloxy group as a substituent group, an alicyclic group of 3 to 7 carbon atoms, or a phenethyl group.

2. A thiazolo[3,2-a]pyrimidine compound according to claim 1, wherein R in the above-mentioned formula (I) is a phenyl group, a benzyl group which has a chlorine atom, a fluorine atom or a bromine atom as a substituent group, a cyclohexyl group or a phenethyl group.

3. A thiazolo[3,2-a]pyrimidine compound according to claim 1, wherein R in the above-mentioned formula (I) is a chlorobenzyl group or a chlorophenyl group.

4. A process for the preparation of a thiazolo[3,2-a]pyrimidine compound expressed by the following formula (I)

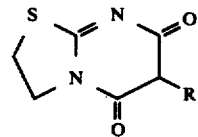

where R represents a phenyl group or benzyl group which has a halogen atom, a lower alkyl or lower alkyloxy group as a substituent group, an alicyclic group of 3 to 7 carbon atoms, or a phenethyl group, comprising cyclizing a compound expressed by the following formula (II) by application of heat

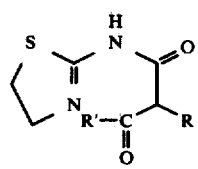

where the definition of R is the same as that given in the case of the above-mentioned formula (I) and R' represents a halogen atom or a lower alkyloxy group.

5. A process for the preparation of a thiazolo[3,2-a]pyrimidine compound according to claim 4, wherein R' in the above-mentioned formula (II) is a methoxy group or an ethoxy group.

6. An immunoregulation drug containing an effective amount of a thiazolo[3,2-a]pyrimidine compound expressed by the above-mentioned formula (I) of claim 1 as an immunoregulating active ingredient.

* * * * *